US009980855B2

(12) United States Patent
Hansson et al.

(10) Patent No.: US 9,980,855 B2
(45) Date of Patent: May 29, 2018

(54) CONSISTENT BLOCKING EARMUFF

(75) Inventors: Fredrik Hansson, Helsinborg (SE);
Claes Haglund, Angelholm (SE)

(73) Assignee: Honeywell Safety Products USA, Inc.,
Smithfield, RI (US)

( * ) Notice: Subject to any disclaimer, the term of this patent is extended or adjusted under 35 U.S.C. 154(b) by 1703 days.

(21) Appl. No.: 11/804,393

(22) Filed: May 17, 2007

(65) Prior Publication Data

US 2007/0226877 A1    Oct. 4, 2007

Related U.S. Application Data

(63) Continuation-in-part of application No. PCT/SE2005/001724, filed on Nov. 16, 2005.

(30) Foreign Application Priority Data

Nov. 17, 2004  (SE) .......................................... 402799

(51) Int. Cl.
*A42B 1/06*    (2006.01)
*A61F 11/14*   (2006.01)

(52) U.S. Cl.
CPC ................... *A61F 11/14* (2013.01)

(58) Field of Classification Search
USPC ..... 2/423, 203, 209, 906; 128/864, 866, 867
See application file for complete search history.

(56) References Cited

U.S. PATENT DOCUMENTS 3,535,710 A * 10/1970 Aileo ................................ 2/209
3,952,158 A *  4/1976 Kyle et al. ...................... 381/72
4,057,856 A    11/1977 Aho
4,459,707 A *  7/1984 Stallings .......................... 2/209
4,523,661 A *  6/1985 Scalzo et al. ................. 181/129
5,241,971 A *  9/1993 Lundin .......................... 128/864
5,920,911 A *  7/1999 Cushman .......................... 2/209
5,996,123 A * 12/1999 Leight et al. ..................... 2/209
6,353,938 B1 *  3/2002 Young ............................... 2/209
7,444,687 B2 * 11/2008 Sato et al. ........................ 2/209
2006/0015989 A1*  1/2006 Faussett et al. .................. 2/423
2006/0212998 A1*  9/2006 Gath ................................. 2/423

FOREIGN PATENT DOCUMENTS

AU    2005307157 B2    4/2009
BR    PI0517728 A      10/2008
CH       659772 A5      2/1987
(Continued)

OTHER PUBLICATIONS

Office Action, Japan Patent Application No. 2007-542973 (English translation attached); 6 pages.
(Continued)

*Primary Examiner* — Sally Haden
(74) *Attorney, Agent, or Firm* — Wick Phillips Gould & Martin LLP

(57) ABSTRACT

An earmuff (3) includes a disc-shaped elastomeric pressure-equalizing element (6') that lies between an inner end of a cup (4) and an outer face of an annular element (7). The elastomeric element (6') is found to provide a more consistent blocking of environmental sound. The cup inner end has a radial projection (15) that projects into a recess (19), and the elastomeric element is bent to lie between the projection and the walls of the recess.

20 Claims, 2 Drawing Sheets

(56) References Cited

FOREIGN PATENT DOCUMENTS

| | | | |
|---|---|---|---|
| CN | 2513549 | Y | 10/2002 |
| CN | 100508921 | C | 7/2009 |
| DE | 8801284 | U1 | 5/1988 |
| EP | 1811932 | B1 | 8/2009 |
| GB | 2130470 | A | 6/1984 |
| JP | 05501068 | A | 3/1993 |
| JP | 06-007397 | | 1/1994 |
| JP | 2008520337 | A | 6/2008 |
| SE | 514555 | C2 | 3/2001 |
| SE | 530035 | C2 | 2/2008 |
| WO | 2006054944 | A1 | 5/2006 |

OTHER PUBLICATIONS

International Application No. PCT/SE2005/001724, International Search Report, dated Feb. 28, 2006, 3 pages.
International Application No. PCT/SE2005/001724, Written Opinion of the International Searching Authority, dated Feb. 28, 2006, 4 pages.
International Application No. PCT/SE2005/001724, International Preliminary Report on Patentability, dated May 22, 2007, 5 pages.
Europe Patent Application No. 05803618.7, Extended European Search Report, dated Oct. 6, 2008, 3 pages.
Europe Patent Application No. 05803618.7, Intention to Grant, dated Jan. 28, 2009, 4 pages.
Europe Patent Application No. 05803618.7, Intention to Grant, dated Jul. 16, 2009, 2 pages.

* cited by examiner

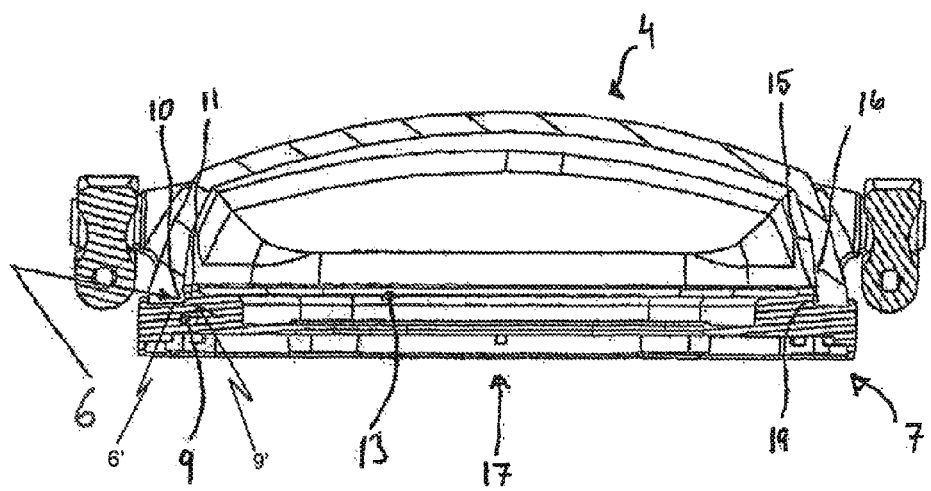
FIG 3
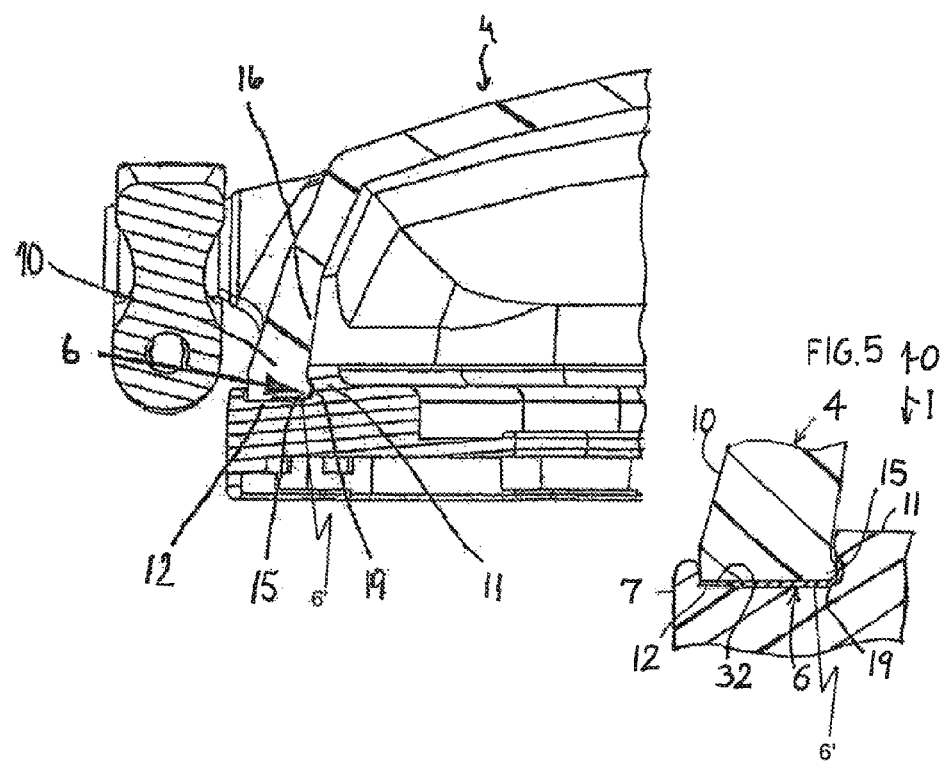
FIG 4
FIG.5

CONSISTENT BLOCKING EARMUFF

CROSS REFERENCE

This is a continuation-in-part of PCT/SE2005/001724 filed 16 Nov. 2005, which claimed priority from Swedish patent application NO. 0402799-1 filed 17 Nov. 2004.

FIELD OF THE INVENTION

The present invention relates generally to an earmuff comprising a cup-shaped cap, which has an edge portion defining an opening, and an annular element which is arranged to extend along said edge portion, the cup-shaped cap and the annular element being secured to one another by a locking means.

BACKGROUND OF THE INVENTION

A common type of hearing protector comprises two earmuffs and a headband connecting the earmuffs to one another.

A conventional earmuff usually comprises a cup-shaped cap, an annular bottom plate, a padded sealing ring which is connected to the bottom plate and arranged to abut against a user's head, and stuffing which can be made of foam plastic and is positioned in the cap. The cup-shaped cap and the annular bottom plate are tightly fixed to each other by a conventional snap lock. A conventional snap lock is provided, for instance, by the cap being provided with a projection extending along the opening portion of the cap. The projection is formed on the inside of the opening portion of the cap. The bottom plate has a connecting portion which is arranged to extend a certain distance into the opening portion of the cap. The connecting portion has on the outside a circumferential groove. The groove cooperates with the projection to tightly hold the cap and the bottom plate together.

However, it has been found that two earmuffs which have been manufactured in the same way according to the description above have a tendency to exhibit different damping properties for sound in different frequency ranges. Differences in damping mean that a first earmuff damps sound within a certain frequency range quite well while at the same time a second earmuff damps sound within the same frequency range relatively poorly.

This means in turn that there is a risk that the two earmuffs in one and the same hearing protector exhibit different sound damping capacities, which means that a user catches a certain sound in one way by one ear and in another way by the other ear. This is a drawback since a user has difficulty in determining the direction of sound, which may cause danger on a shop floor.

Owing to the difference, it is also difficult to adjust an earmuff to a specific purpose. To adjust an earmuff to a specific purpose means, for instance, satisfying a requirement that the capacity of damping sound in a certain frequency range be improved. The problem is, among other things, that different earmuffs of the same type damp, as mentioned above, sound in a certain frequency range to different degrees. An adjustment of an earmuff so that it has a good capacity of damping sound in a first frequency range means, in practice, that it is necessary to accept an inferior damping capacity in a second frequency range. The difference in the damping capacity of different earmuffs of the type described above can very well be in the same order as the distance between said first and second frequency ranges.

SUMMARY OF THE INVENTION

In view of that stated above, an object of the present invention is to provide an improved earmuff.

A special object of the invention is to provide earmuffs which have a consistent sound damping capacity. By consistent sound damping capacity is meant, for instance, that two earmuffs which are of the same type and have been manufactured in the same way have essentially the same sound damping capacity. A further object of the invention is to provide an earmuff which has improved sound damping capacity.

Another object of the invention is to provide a basic construction of an earmuff which allows great freedom in design.

To achieve at least one of the above objects, and also other objects that will be evident from the following description, an earmuff as claimed in claim 1 is provided according to the invention, preferred embodiments being stated in the dependent claims.

In particular an earmuff is provided, comprising a cup-shaped cap, which has an edge portion defining an opening, and an annular element which is arranged to extend along said edge portion, the cup-shaped cap and the annular element being secured to one another by a locking means. The earmuff is characterized in that it further comprises at least one pressure-equalizing means, which is arranged between and in contact with the cup-shaped cap and the annular element.

As a result, an improved earmuff is provided, in which tension or pressure between the cup-shaped cap and the annular element is distributed substantially uniformly around the opening portion of the cap. Effects of differences with respect to geometry, rigidity or the like which, for instance, arise in manufacture and which would result in differences in the transmission of sound between the cap and the annular element are eliminated to a great extent owing to the pressure-equalizing means. A particular advantage of the inventive earmuff is that two earmuffs achieve a similar sound damping capacity. A further advantage is that the earmuff can be adjusted to different surroundings and to sound in specific frequency ranges. It also brings the advantage that a user perceives sound in the same way by both ears, which is advantageous since it will be easier to identify where a source of sound is positioned.

It should be noted that annular is not necessarily limited to a circular shape, but the ring shape defines an element which extends around a central opening. The ring shape can be more or less square or have other shapes. The annular element can be formed with different cross-sectional shapes depending on what other components it is arranged to cooperate with.

Said at least one pressure-equalizing means is arranged in an engaging surface between the cup-shaped cap and the annular element of said locking means. By the pressure equalizing means being arranged in an engaging surface, it will provide a pressure-equalizing sound transmission between the cap and the annular element, which adds to consistent transmission of sound.

The engaging surface defines a geometric band extending along the opening and having a width, the pressure equalizing means being arranged to extend along the opening along a first portion of the width of the engaging surface. By the pressure-equalizing means extending along the opening, consistent force transmission is obtained along the entire circumference of the cap and the annular element.

The cup-shaped cap and the annular element can, along a second portion of the width of the engaging surface, abut directly against each other, which brings the advantage of obtaining a dimensionally stable contact between the cap and the annular element.

The pressure-equalizing means may comprise an annular element, which brings the advantage that the pressure equalizing means can be manufactured in a simple manner. By annular is meant that the pressure-equalizing means has in the longitudinal direction the shape of a ring. This also means that the pressure-equalizing means helps to ensure tightness in the connection between the cup-shaped cap and the annular element. Thus the tolerances in the manufacture of the cup-shaped cap and the annular element can be increased.

The pressure-equalizing means may comprise an elastic insert, which means that the pressure-equalizing means can be manufactured in a simple and inexpensive manner. In addition, the elastic insert may help to maintain tension in the locking means.

The elastic insert can be made of a polymer material, which brings the advantage that it can be manufactured in a simple and inexpensive manner.

To fasten the cup-shaped cap and the annular element to one another in a simple, inexpensive and time-effective manner, the locking means may comprise a snap lock.

By snap lock is meant a lock comprising two parts. In locking, one of the parts is pressed onto the other part and snaps, by temporary elastic deformation, onto this other part and locks the two parts relative to one another. In a preferred embodiment, a snap lock is provided by the cap being provided with a projection which extends along the opening portion of the cap. The projection is formed on the inside of the opening portion of the cap. The annular element has a flange which is arranged to extend a certain distance into the opening portion of the cap. The flange has on its outside a circumferential recess. The recess cooperates with the projection to tightly hold the cap and the annular element together.

The pressure-equalizing means can be arranged in said recess. The location of the pressure-equalizing means brings the advantage that it simplifies mounting since it easily retains its position in the recess. It also brings the advantage that the pressure-equalizing means is located in the position in which the greatest power transmission between the cap and the annular element usually occurs.

The elastic insert can have a circular, square, triangular or H-shaped cross-section. The elastic insert can have a homogeneous or hollow cross-section, such as a tube of various cross-sectional shapes.

The novel features of the invention are set forth with particularity in the appended claims. The invention will be best understood from the following description when read in conjunction with the accompanying drawings.

BRIEF DESCRIPTION OF THE DRAWINGS

A preferred embodiment of the present invention will now be described by way of example and with reference to the accompanying drawings.

Components having a similar function have been given the same reference numerals throughout the text.

FIG. 3 is a cross-sectional view of the earmuff in FIG. 1 along line I-I, without the sealing ring.

FIG. 4 is a cross-sectional view of an enlarged part of FIG. 3.

FIG. 5 is an enlarged view of a portion of FIG. 4.

DESCRIPTION OF THE PREFERRED EMBODIMENTS

Figure 1:
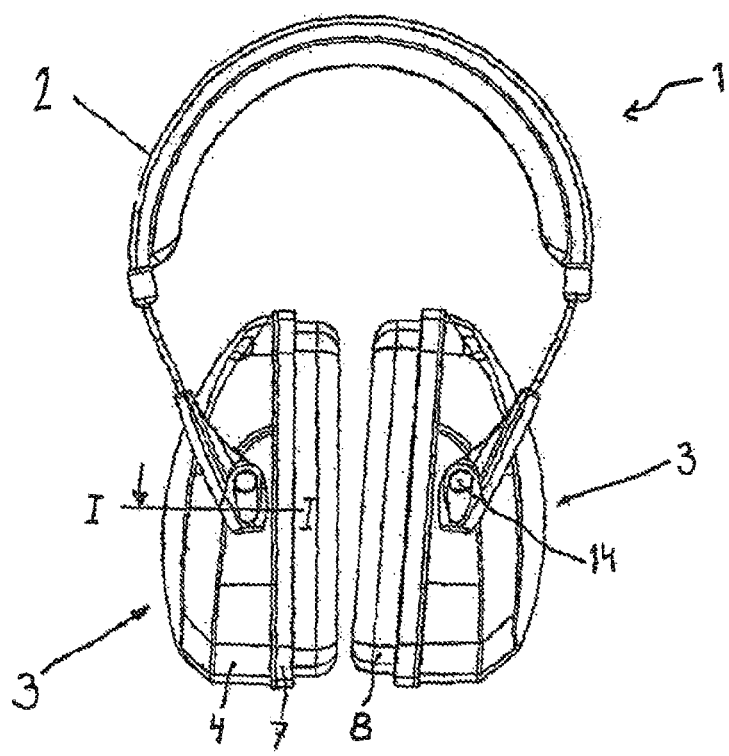
FIG. 1 is a side view of a hearing protector comprising two inventive earmuffs.

FIG. 1 illustrates a hearing protector 1 comprising a headband 2 and two earmuffs 3. The earmuffs 3 are connected to the respective ends of the headband 2. In use, a user (not shown) places an earmuff 3 over each ear, the headband 2 holding the earmuffs 3 in place on the user's head.

Figure 2:
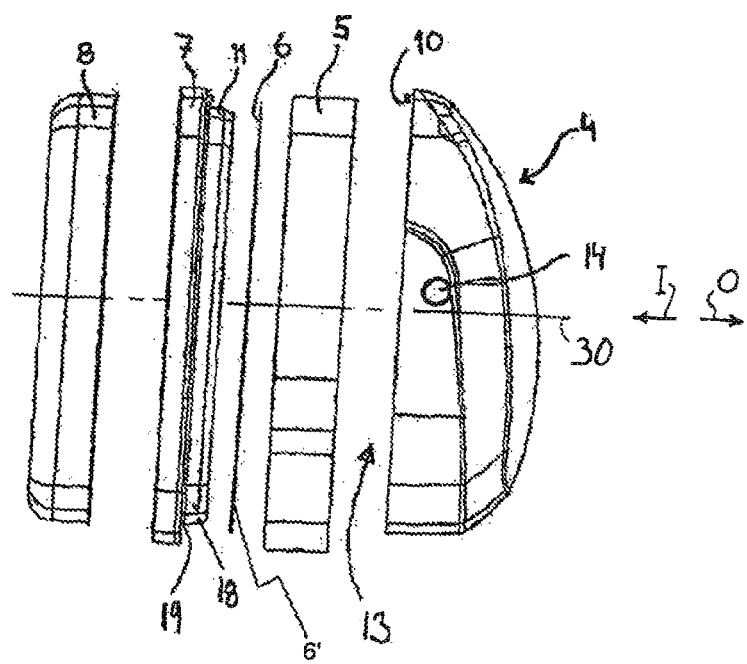
FIG. 2 is an exploded view of an inventive earmuff.

FIG. 2 shows that the earmuff includes a ring 5 of stuffing material that blocks sound and that fits into a rigid cap 4. The cap 4 has an inner (inward-facing—I) part 10 (which can also be referred to as cap inner end and first part) that previously directly abutted a rigid annular element 7. FIG. 2 also shows the outer direction (O) for reference. A radial projection 15 (FIG. 5) on the cap inner part 10 snaps into a radial recess 19 in a part 11 of the annular element. The radial projection 15 and radial recess 19 each extends at least partially radial to the earmuff axis 30. It appears that this construction previously left a small gap through which sound could pass, with the frequency of sound that could pass depending on the exact shape and size of the gap.

In the present invention, applicant places a pressure equalizing means (such as an elastomeric disc, by way of nonexclusive example) 6 (an elastomer is a material with a Young's modules of elasticity of under 50,000 psi) in the space between the flat cap end 10 and a flat surface of annular element 7. Also, part of the elastomeric disc lies between the projection 15 and recess 19. When the cap 4 and annular element 7 are snapped together, the elastomeric ring is compressed. This seals the space between the cap end and the annular element. It is found that the presence of the compressed elastomeric disc, or pressure equalizing means, results in blocking sounds of all frequencies, far more uniformly than in the prior art when the elastomeric ring was not used. As a result, the amplitude of sound of all frequencies that reach the wearer's two ears, is much more equal than in the prior art. This avoids a condition in which the wearer cannot determine the direction from which a sound came.

The elastomeric disc, or ring-shaped member lies between flat facewise-adjacent surfaces 12, 32 of the cap inner (e.g. inward-facing) end 10 and of the annular member 7.

An earmuff 3 is shown in more detail in FIGS. 2-4, to which reference is now made. The earmuff 3 comprises a cup-shaped cap 4, stuffing material 5, a pressure equalizing means 6, an annular element 7 and a sealing ring 8. The stuffing material 5 is arranged in the cavity of the cup-shaped cap 4. A farther side, the side facing away from a user, of the annular element 7 is fixed to the cup-shaped cap 4 by a locking means 9 in the form of a snap lock 9'. The snap lock 9' comprises a first and a second part 10, 11. The first part 10 is positioned on the cup-shaped cap 4 and the second part 11 is positioned on the annular element 7. The pressure-equalizing means 6 is positioned in an en aging surface between, and is in contact with, both the first and the second parts 10, 11 of the snap lock 9', see FIG. 3 and FIG. 4. The sealing ring 8 is fixed by a second snap lock (not shown) to a front side, the side facing a user, of the annular element 7.

The cap 4 is in the form of a cup and has an edge portion 12 which defines an opening 13 of the cap. As shown in FIG.

2 and FIG. 3, the opening 13 of the cap 4 defines a space which resembles a space as enclosed by a half-sphere.

On the outside of the cap 4, that is the side facing away from the user and from the enclosed space, two fastening means 14 are positioned. The fastening means 14, which can be, for instance, two pins, are arranged to fasten the headband 2 to the cap 4.

On the inside of the cap 4, that is the side facing a user and the enclosed space, the first part 10 of said snap lock 9' is positioned. The first part 10 comprises a projection 15 which extends around the inside of an opening portion 16 of the cap 4. The opening portion 16 has an engaging surface which in the assembled state is adapted to engage and abut against on the one hand the pressure equalizing means 6 and, on the other, a corresponding engaging surface of the second part 11 of the snap lock 9'.

In the example shown, the projection 15 and the cap 4 are made in one piece of a polymer material. It will be appreciated that the parts can be separately made and subsequently assembled in a suitable manner, for instance by welding or gluing.

The annular element 7 has a front side and a rear side, the front side being the side facing the sealing ring 8 and thus also a user, and the rear side being the side facing the cap 4 and thus also facing away from a user. The annular element 7 which is called bottom plate has a through hole 17 extending from the front side to the rear side.

The second part 11 of the snap lock 9' is formed on the rear side of the annular element 7. The second part 11 extends as a circumferential flange 18 around the annular element 7. The second part 11 has an extent corresponding to the shape of the opening 13 of the cup-shaped cap 4. A recess 19 is formed on the side of the flange 18 which faces away from the through hole 17. The recess 19 has a shape supplementary to the projection 15 of the cup-shaped cap 4. On the same side as the recess 19, the flange 18 has an engaging surface. In FIGS. 2-4, the surface of the recess 19 is included in the engaging surface, which in the assembled state is in contact with the pressure-equalizing means 6 and the engaging surface of the cap 4. It should be mentioned that the second part 11 can be formed with a smaller height relative to corresponding parts according to prior art, which brings the advantage that the requirements as to the shape of the cap 4 are reduced.

The pressure-equalizing means 6 consists in the shown example of an annular flexible insert 6'. The insert 6' is circular. The insert 6' is arranged between the cup-shaped cap 4 and the annular element 7. The insert 6' is in contact with both the cup-shaped cap 4 and the annular element 7 in the respective engaging surfaces. The location of the pressure-equalizing means 6 between the cup-shaped cap 4 and the annular element 7 results in the pressure between the first and the second part 10, 11 of the snap lock 9' being equalized. The pressure-equalization results in the effect of any irregularities in the first and the second part 10, 11 of the snap lock 9' being eliminated or in any case reduced. The pressure-equalizing means 6 also brings the advantage that the tolerances in the manufacture of the cup-shaped cap 4 and the annular element 7 can be increased, which results in reduced costs of manufacture. The reason for this is that the pressure-equalizing means 6 also helps to provide a seal between the cap 4 and the annular element 7.

The pressure-equalizing means 6 is positioned in the recess 19 of the second part 11 of the annular element 7, which is illustrated in FIG. 3 and FIG. 4. In the mounted state, the projection 15 of the snap lock 9' of the cap 4 presses the pressure-equalizing means 6 against the walls of recess 19 of the snap lock 9' of the annular element 7.

It will be appreciated that the present invention is not limited to the embodiments described above and that a person skilled in the art can modify the above-described earmuff within the scope of the invention as defined in the claims.

For instance, it is possible to place the elastic insert also outside the recess which is adapted to provide the snap lock function. In such an embodiment, the flange of the annular portion is advantageously provided with a further groove which is adapted to accommodate the annular elastic insert.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An earmuff comprising a cup-shaped cap, which has an edge portion defining an opening, and an annular element which is arranged to extend along said edge portion, the cup-shaped cap and the annular element being secured to one another by a locking means,
    wherein the earmuff further comprises at least one pressure-equalizing means, which is arranged between and in contact with the edge portion of the cup-shaped cap and the annular element, wherein
    said at least one pressure-equalizing means being arranged in an engaging surface of said locking means, said engaging surface being arranged between the cup-shaped cap and the annular element, and wherein
    the engaging surface extending along the opening and having a width, the pressure-equalizing means being arranged to extend along the opening along a first portion of the width of the engaging surface.

2. An earmuff as claimed in claim 1, wherein the cup-shaped cap and the annular element abut directly against one another along a second portion of the width of the engaging surface.

3. An earmuff as claimed in claim 1, wherein the pressure-equalizing means is an elastomeric disc, and wherein the elastomeric disc is compressed between the annular element and the edge portion of the cup-shaped cap.

4. An earmuff as claimed in claim 1, wherein the pressure-equalizing means comprises an elastic ring.

5. An earmuff as claimed in claim 1, wherein the pressure-equalizing means is made of a polymer material.

6. An earmuff as claimed in claim 1, wherein the locking means comprises a snap lock.

7. An earmuff as claimed in claim 6, wherein the engaging surface of the locking means comprises an engaging surface of the cup-shaped cap and an engaging surface of the annular element, and wherein the snap lock comprises a projection located in the engaging surface of the cup-shaped cap and a recess located in the engaging surface of the annular element, and wherein the pressure-equalizing means being arranged in said recess.

8. An earmuff as claimed in claim 6, wherein the pressure-equalizing means comprises an elastomeric ring which is compressed between the edge portion of the cup-shaped cap and the annular element by the snap lock.

9. An earmuff as claimed in claim 8, wherein the elastomeric ring lies between and in contact with flat facewise-adjacent surfaces of the cup-shaped cap edge portion and the annular element.

10. An earmuff as claimed in claim 1 further comprising stuffing material operable to block sound located within the cup-shaped cap.

11. An earmuff comprising a cup-shaped cap, which has an edge portion defining an opening, and an annular element which is arranged to extend along said edge portion, the cup-shaped cap and the annular element being secured to one another by a locking means;
    wherein the cup-shaped cap edge portion comprises an inward-facing cap end; and
    wherein the earmuff further comprises at least one pressure-equalizing means arranged between and in contact with both the cap end of the cup-shaped cap and the annular element.

12. The earmuff of claim 11, wherein the pressure-equalizing means comprises an elastic insert and wherein the elastic insert lies between and in contact with flat, facewise-adjacent surfaces of both the annular element and the cap end.

13. An earmuff as claimed in claim 11, wherein the locking means is a snap lock formed by an engaging surface of the cap end and an engaging surface of the annular element; wherein the pressure-equalizing means is arranged between and in contact with both the engaging surface of the cap end and the engaging surface of the annular element; and wherein the location of the pressure-equalizing means between the engaging surfaces of the annular element and the cap end provides a seal between the annular element and the cap end.

14. An earmuff as claimed in claim 13, wherein the engaging surface of the cap end comprises a radial projection and the engaging surface of the annular element comprises a radial recess; and wherein the pressure equalizing means comprises an elastomeric ring located between the radial projection and the radial recess.

15. An earmuff as claimed in claim 11 wherein the locking means comprises an engaging surface of the cap end and an engaging surface of the annular element, wherein the engaging surfaces extend along the opening and have a width, the pressure-equalizing means being arranged to extend along the opening along a first portion of the width of the engaging surfaces.

16. An earmuff as claimed in claim 11 wherein the at least one pressure-equalizing means comprises an elastomeric disc or an elastomeric ring.

17. An earmuff comprising a cup-shaped cap, which has an edge portion defining an opening, and an annular element which is arranged to extend along said edge portion, the cup-shaped cap and the annular element being secured to one another by a locking means;
    wherein the earmuff further comprises at least one pressure-equalizing means arranged between and in contact with the edge portion of the cup-shaped cap and the annular element.

18. The earmuff as claimed in claim 17, wherein the locking means is formed by an engaging surface of the edge portion of the cup-shaped cap and an engaging surface of the annular element; and wherein the pressure-equalizing means is arranged between and in contact with at least a portion of the engaging surface of the edge portion of the cup-shaped cap and at least a portion of the engaging surface of the annular element.

19. The earmuff of claim 18, wherein the pressure-equalizing means comprises an elastic ring or disc.

20. The earmuff of claim 17, wherein the pressure-equalizing means distributes pressure in the locking means substantially uniformly around the opening of the cup-shaped cap by compression of the pressure-equalizing means between flat facewise-adjacent engaging surfaces of the annular element and the edge portion of the cup-shaped cap.

* * * * *

UNITED STATES PATENT AND TRADEMARK OFFICE
CERTIFICATE OF CORRECTION

PATENT NO.           : 9,980,855 B2
APPLICATION NO.      : 11/804393
DATED                : May 29, 2018
INVENTOR(S)          : Hansson et al.

Page 1 of 1

It is certified that error appears in the above-identified patent and that said Letters Patent is hereby corrected as shown below:

On the Title Page

Item (74), Line 2: insert --,-- after "Martin"

In the Specification

Column 4, Line 61: "en aging" should be "engaging"

In the Claims

Column 7, Line 1: insert --,-- after "1"

Column 7, Line 36: insert --,-- after "11"

Column 8, Line 6: insert --,-- after "11"

Signed and Sealed this
Fourteenth Day of August, 2018

Andrei Iancu
*Director of the United States Patent and Trademark Office*